United States Patent

Jameison et al.

[11] Patent Number: 6,136,233
[45] Date of Patent: Oct. 24, 2000

[54] HYDROGEN PEROXIDE BASED ECL

[75] Inventors: Fabian Jameison, Gaithersburg; Jonathan K. Leland, Silver Spring, both of Md.

[73] Assignee: IGEN International, Inc., Gaithersburg, Md.

[21] Appl. No.: 09/137,159

[22] Filed: Aug. 20, 1998

Related U.S. Application Data

[63] Continuation of application No. 08/482,352, Jun. 7, 1995.
[51] Int. Cl.[7] .............................. C09K 3/00; C09K 11/06; C12Q 1/00
[52] U.S. Cl. ...................... 252/700; 252/583; 252/519.2; 252/519.21; 252/301.18; 252/408.1; 435/4; 435/5; 435/6; 436/805
[58] Field of Search .............................. 252/700, 519.2, 252/519.21, 301.18, 583, 408.1; 435/4, 5, 6; 436/805

[56] References Cited

U.S. PATENT DOCUMENTS 5,308,754  5/1994  Kankare et al. .................. 436/805
5,527,710  6/1996  Nacamulli et al. .................. 435/4

OTHER PUBLICATIONS

Jameison et al., Anal. Chem., vol. 68, pp. 1298–1302, (1996).

Kazakov et al., Chemical Abstracts 88:81303, Abstract of Opt. Spek Trosk, vol. 43, No. 6, pp. 1081–1085, (1977).

Rubenstein et al., J. Am. Chem. Soc., vol. 103, pp. 512–516, (1981).

*Primary Examiner*—Philip Tucker
*Attorney, Agent, or Firm*—Whitman Breed Abbott & Morgan LLP

[57] ABSTRACT

An electrochemiluminescence (ECL)-based assay for the quantitation of classical clinical chemistry analytes, where glucose, ethanol, carbon dioxide, cholesterol, as $H_2O_2$ liberating systems coupled to a tris(bipyridyl)ruthenium(II) $Ru(bpy)_3^{2+}$ luminophore generate an ECL signal, which can be detected spectrophotometrically or electrochemically. The $H_2O_2$ present reacts with oxalate in the presence of $Ru(bpy)_3^{2+}$ to give an ECL response.

8 Claims, 7 Drawing Sheets

HYDROGEN PEROXIDE BASED ECL

This application is a continuation of application Ser. No. 08/482,352, filed Jun. 7, 1995 now allowed, which is incorporated herein by reference.

FIELD OF THE INVENTION

The present invention relates to electrogenerated chemiluminescent (ECL) reactions for detecting, analyzing and monitoring analytes. These reactions are based upon an initial reaction of a reductant and hydrogen peroxide ($H_2O_2$), which further react in a redox fashion with a luminophore, resulting in ECL detection of the analyte. More specifically, the present invention relates to the analysis and detection of analytes that form or consume $H_2O_2$ by allowing the analytes to react with reductant, such as $C_2O_4^{2-}$ (oxalate), in the presence of a luminophore, such as, tris (2,2'-bipyridyl) ruthenium(II), $Ru(bpy)_3^{2+}$. Electrochemical oxidation of the remaining oxalate produces the carbon dioxide radical anion (reductant) that reacts with the oxidized luminophore to give an excited state ruthenium(II) (bpy)$_3$ complex, resulting in an ECL signal, the intensity of which is inversely proportional to the concentration of the analyte present.

BACKGROUND OF THE INVENTION

Numerous techniques are available to the skilled practitioner for detecting or monitoring hydrogen peroxide present as a reactant or treating agent in a chemical process or which represents an analyte in a diagnostic protocol. The hydrogen peroxide that is to be monitored may be added directly into the system and its depletion subsequently monitored, or it may be formed from the systems' reactants, with or without catalysts.

Hydrogen peroxide is used and monitored in metal extraction processes; decomposition of alkyl phosphates; synthesis of sulfonic acids and carboxylic acid ester derivatives thereof, oxidation processes, and sterilization systems. In the diagnostic area, hydrogen peroxide is often used to indirectly indicate the presence or absence of an analyte of interest. Such analytes include, but are not limited to, cholesterol, glucose, uric acid, ascorbic acid, triglycerides, and thiol compounds.

Prior methods for the detection and quantitation of such peroxide-forming analytes were calorimetric and/or spectrophotometric (Allain, C. C., et. al., cf. cholesterol reprint). For example, in U.S. Pat. No. 4,238,195 (Boguslaski, et al.) the excitation of a label is preferably accomplished by exposure to a substance, such as a high energy intermediate produced by the reaction between hydrogen peroxide and highly reactive materials such as oxalyl chloride, oximides and bis-oxalate esters. The mechanism of the Boguslaski system would appear to result from the reaction of hydrogen peroxide and various reactive bis-oxalate esters to form a high energy intermediate believed to be, for example, 1,2-dioxethanedione or activated carbon dioxide. The high energy intermediate then transfers energy to a fluorescer which thereafter emits light with a spectrum essentially similar to its normal fluorescent spectrum. The electromagnetic radiation released can be in the infra red, visible, or ultraviolet range, and the fluorescer-label is neither a consumable reactant nor is altered chemically in any way during the reaction.

U.S. Pat. No. 4,372,745 to Mandle, et al. relates to chemical luminescence amplification substrate systems for amino acid chemistry involving microencapsulated fluorescers. Mandle discusses prior art techniques where hydrogen peroxide, an essential component in many chemiluminescent reactions, is the specie selected for use in detecting the analyte of interest. For example, Mandle discusses the prior art oxidation of glucose with glucose oxidase as a source of $H_2O_2$ which, in turn, is reacted with luminol to produce chemiluminescence in proportion to the initial glucose concentration. However, a limit of detection of $10^{-8}$M peroxide is obtained using this technique. To overcome the $H_2O_2$ dependence of the prior art, Mandle uses the large chemiluminescent reservoir of energy obtained in the oxalate system chemistry by adding a suitable quantity of hydrogen peroxide and oxalate.

In U.S. Pat. No. 4,396,579, Schroeder discusses that the mechanism of organic chemiluminescence in solution involves three stages: (1) a first preliminary reaction to provide an intermediate; (2) an excitation step in which the chemical energy of the intermediate is converted into excitation energy; and (3) emission of light from the excited product formed in the chemical reaction.

U.S. Pat. No. 4,647,532, Wantanabe, et al. relates to methods for determining hydrogen peroxide by chemiluminescence where a non-fluorescent substance and hydrogen peroxide are reacted in the presence of an oxidizing catalyst which produces a fluorescent substance and water. Thereafter, the fluorescent substance reacts with an oxalic acid ester in the presence of hydrogen peroxide to produce light. The oxidizable non-fluorescent substance used in the Wantanabe process are related to fluorescein and its derivatives.

In U.S. Pat. No. 4,994,377 (Nakamura, et al.), 1,5-anhydroglucitol is assayed by monitoring the hydrogen peroxide and in U.S. Pat. No. 5,093,238 (Yamashoji, et al.) determine the density or activity of viable cells by incubating the viable cells in the presence of a quinone whose reduced form reduces dissolved oxygen resulting in the formation of hydrogen peroxide. The hydrogen peroxide is reacted with a chemiluminiscent reagent in the presence of a fluorescent substance to cause fluorescence.

In U.S. Pat. No. 5,238,610 to Thompson a peroxy oxalate chemiluminiscent detection method is proposed which is more suitable for aqueous systems and relies upon a microemulsion. The fluorescent compounds used in the Thompson system are anthracene, napthacene, naphthalene, aminopyrine, dansyl amino acids, fluorescein and rhodamine derivatives. The drawback of calorimetric analysis is the necessity to monitor at different wavelengths (either in the visible or ultraviolet range) depending on the nature of the analyte.

A number of clinically important diagnostic tests are based on enzyme-coupled conversions involving the cofactors $NAD^+/NADH$, $NADP^+/NADPH$. These detection methods are spectrophotometric in nature, wherein the amount of reduced cofactor produced or consumed is directly proportional to the quantity of analyte. Colorimetric methods where one product of a particular transformation is hued (e.g. p-nitrophenol), or as with hydrogen peroxide, is enzymatically coupled to chromogenic agents (o-dianisidine, 4-aminoantipyrine) have been used. The resulting dye, i.e., quinoneimine dyes, are detected using spectrophotometric techniques.

In contrast to calorimetric methods, electrochemiluminescence (ECL) exploits the highly sensitive light-emitting property of a luminophore, such as tris(2,2'-bipyridyl) ruthenium(II), $Ru(bpy)_3^{2+}$, and the strong reductive nature of an amine such as tripropylamine (TPrA). The use of luminescent metal labels for ECL detection is discussed in U.S. Pat. No. 5,221,605 to Bard, et al. incorporated herein by reference. Bard, et al. refer to the Mandle patent discussed above and indicates that Mandle discloses the use of chemiluminescent labels in amino acid chemical applications where the labels are excited into a luminescent state by chemical means, such as by reaction of the label with $H_2O_2$ and an oxalate. In these systems, $H_2O_2$ oxidatively converts the oxalate into a high energy derivative, which then excites the label. Bard, et al. express the opinion that the Mandle system, in principle, should work with any luminescent material that is stable in the oxidizing condition of the assay and can be excited by the high energy oxalate derivative. Unfortunately, this very versatility is a source of a major limitation of the technique because "typical biological fluids containing the analyte of interest also contain a large number of potentially luminescent substances that can cause high background levels of luminescence." Bard, et al. also indicate that the work of Rubenstein and Bard (1981), "Electrogenerated chemiluminescence." 37. Aqueous ECL Systems based on Ru(2,2 bipyridine)$_3^{2+}$, an oxalate or organic acids, that demonstrates that bright orange chemiluminescence can be based on the aqueous reaction of chemically generated or electrogenerated Ru (bipyridine)$_3^{3+}$ (where "bpy" represents a bipyridyl ligand) with strong reductants produced as intermediates in the oxidation of oxalate ions or other organic acids. However, Bard, et al. do not suggest a hydrogen peroxide-oxalate ECL system.

The intensely luminescent Ru(bpy)$_3^{2+}$ can be used to quantify other systems including amines, amino acids and proteins. Prior methods for coupling ECL to enzymatic reactions are limited to those using nicotinamide adenine dinucleotide (NADH) cofactor-linked systems. Unfortunately, this technique limits the types of analytes which may be assayed. Prior ECL assays have used oxalate-based ECL, but have not been used to identify $H_2O_2$, alone or from $H_2O_2$ producing and consuming reactions.

A luminol-dependent chemiluminescence reaction has been described (Vilim, V. and Wilhelm, J. Free Radic Biol Med 6(6):623–629 (1989)) for detection of various oxygen species, such as superoxide anions, hydrogen peroxide, and hydroxyl radicals. Although the luminol-dependent chemiluminescence reaction is able to detect oxygen species, the reaction has little ability to discriminate between the various oxygen or radical species.

Thus a need exists for a reaction system that is not wavelength dependent, such as prior art colorimetric techniques, or limited to reactions based upon nicotinamide adenine dinucleotide (NADH) cofactor-linked systems. The current invention, as described hereinafter, provides a system for analyzing a wider variety of analytes to be assayed by using ECL.

Thus, a further need exists for a reaction system that is able to detect the presence of hydrogen peroxide and distinguish hydrogen peroxide from other oxygen species.

SUMMARY OF THE INVENTION

The present invention relates to the detection, analysis or monitoring of $H_2O_2$ that is present in a chemical or analytical process as a reactant which is consumed or generated. In the analytical area, the hydrogen peroxide-producing and -consuming can include, but is not limited to, analytes such as cholesterol, glucose, triglycerides (glycerol-1-phosphate oxidase), lipase-PS (glycerol-1-phosphate oxidase), uric acid (uricase), enzymes (catalase) and other $H_2O_2$-producing and -consuming reactants, analytes or reagents.

The detection and quantitation of these $H_2O_2$-producing and -consuming reactants, analytes or reagents is made possible by monitoring ECL emissions of the $H_2O_2$-oxalate-metal luminophore reaction.

An aspect of the present invention is to provide a chemical or biochemical process where a portion of a chemical or biochemical process stream of the chemical or biochemical process is contacted with a coreactant, and the process stream portion contains at least $H_2O_2$, $H_2O_2$ producing or $H_2O_2$ consuming component(s), where the contacting step is performed in the presence of a ruthenium luminophore and results in the generation of an ECL emission.

Another aspect of the present invention is an ECL emission composition containing (1) an $H_2O_2$-producing or -consuming reactant, (2) a $H_2O_2$ coreactant and (3) a metallic, non-colorimetric luminophore that emits light from the reaction (1)–(3), with the proviso that when (1) contains a $H_2O_2$-consuming reactant, $H_2O_2$ is present.

An object of the present invention is to provide an analytical technique whereby a single set of instrument parameters (e.g. window, PMT, POP etc.) can be used for a multitude of different $H_2O_2$ producing or consuming analytes, reagents, reactants, etc.

A further object of the present invention is to provide a hydrogen peroxide reductant ECL system for use in the analytical or chemical process industry whereby a single instrument may be used for both technological environments.

A still further object of the present invention is to provide an ECL method for detecting $H_2O_2$.

Another object of the present invention is to provide a method of assaying $H_2O_2$-producing or -consuming reactants or substrates.

A further object of the present invention is to provide a method for reacting and detecting $H_2O_2$ wherein an oxalate coreactant is reacted with an $H_2O_2$-forming or -consuming enzymatic or non-enzymatic component and a luminescing metal label in the presence of an electrode and measuring the resulting electrogenerated chemiluminescence.

Another object of the present invention is to provide a non-spectrophotometric method for quantitation of an $H_2O_2$-forming or -consuming analyte by measuring electrogenerated chemiluminescence of the analyte from the reaction of $H_2O_2$ and an oxalate reductant.

A further object of the present invention is to provide a batch or continuous method of assaying hydrogen peroxide via electrogenerated techniques.

These and other objects of the present invention will become evident in view of the following description when considered in conjunction with the non-limiting examples and annexed drawings. These examples are set forth primarily for illustration and any specific enumeration of detail set forth therein should not be interpreted as a limitation on the case except as is indicated in the appended claims.

DETAILED DESCRIPTION OF THE INVENTION

A process for analyzing and detecting analytes of interest that form or consume $H_2O_2$, which is allowed to react with oxalate in the presence of the luminophore is the basis of the present invention. The metal luminophore is preferably tris (2,2'-bipyridyl)ruthenium(II), $Ru(bpy)_3^{2+}$, prepared in accordance with the disclosure of U.S. Pat. No. 5,221,605 to Bard, et al, incorporated herein by reference. The hydrogen peroxide-oxalate-ruthenium system enables selective detection of hydrogen peroxide in chemical processes or analytical systems by electrogenerated chemiluminescent techniques.

Figure 1:
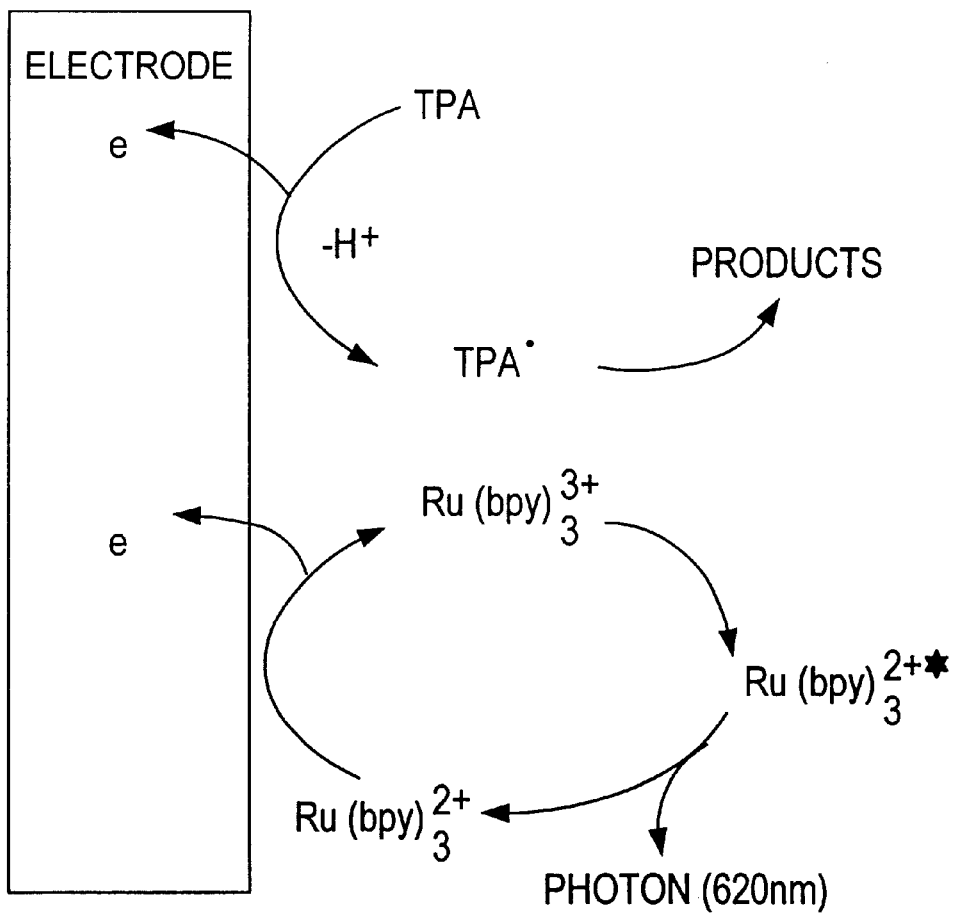
FIG. 1. Shows the mechanism for ECL reaction.

According to the present invention, $H_2O_2$ and an oxalate react and oxidize the luminophore. Electrochemical oxidation of the remaining oxalate produces a carbon dioxide radical anion (reductant) that reacts with the oxidized luminophore to give an excited state ruthenium (II) $(bpy)_3$ complex, resulting in an ECL signal, the intensity of which is inversely proportional to the concentration of the analyte present. Consequently, an excess of oxalate should be added, the quantity of which is readily obtainable by those having the requisite skill in the art. The generic reaction scheme for ECL reaction is shown in FIG. 1, with the reaction scheme of the present invention for ECL is set forth in general terms below:

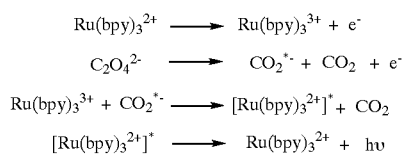

In the chemical process industry, a reaction stream or effluent stream containing hydrogen peroxide is sampled and analyzed. The sampling may be continuous or batch in nature.

In diagnostics, a sample containing the analyte of interest, e.g., hydrogen peroxide, cholesterol, glucose, triglycerides, (glycerol-1-phosphate oxidase), lipase-PS (glycerol-1-phosphate oxidase), and uric acid (uricase) and other $H_2O_2$-producing or consuming substrates, reagents, analytes and/ or reactants, may be sampled batchwise or continuously using available sampling and flow systems. The following reaction schemes exemplify some of the ECL techniques according to the present invention:

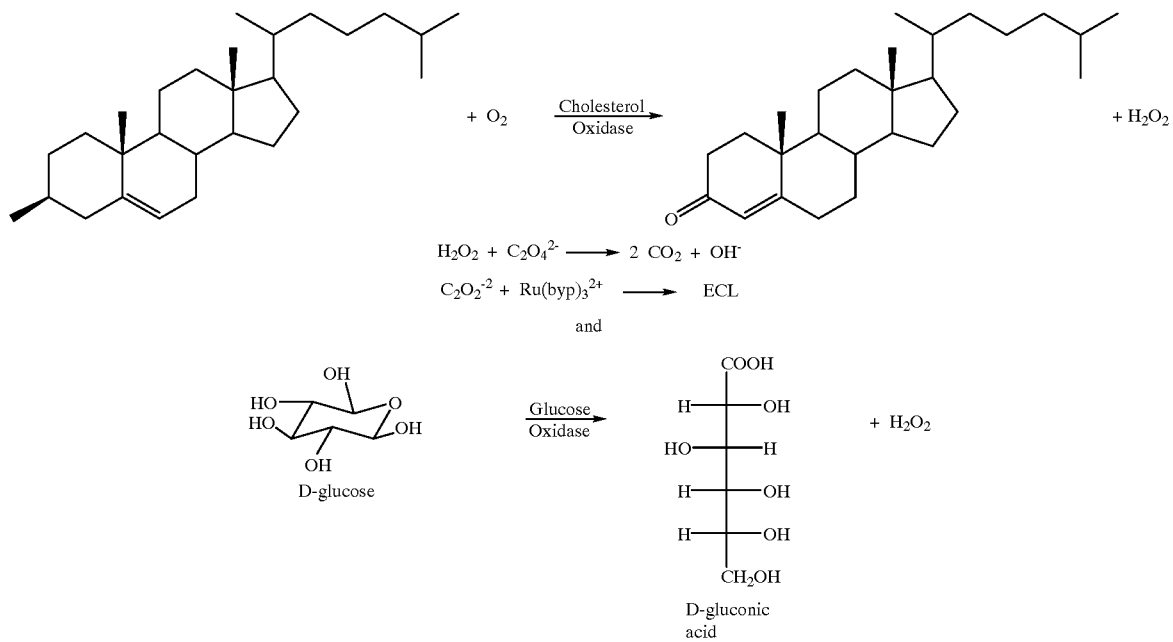

In a preferred embodiment, ECL measurements were made using an Origen™ Analyzer (IGEN, Inc., Rockville, Md.). The instrument integrates a luminometer, a potentiostat, fluid handling components, an electrochemical flow-cell and a 50-tube carousel. Alternatively, a continuous system may be provided whereby a sampling tube is associated with a chemical process and with metering and flow components known in the art conveyed to the flow-cell of the above mentioned IGEN analyzer. The analytical system is controlled by a PC via operator manipulation of on-screen menus. Spectrophotometric measurements were made for comparison purposes and were obtained using a Hitachi model U-3200 Recording Spectrophotometer.

The reagents used in the following, non-limiting examples include cholesterol oxidase (EC 1.1.3.6) from Streptomyces sp. was obtained from Calbiochem (LaJolla, Calif.); catalase (EC1.11.1.6) from bovine liver; glucose oxidase (EC 1.1.3.4) from *Aspergillus niger* and β-D-(+)-glucose and D-glucose-6-phosphate were obtained from Sigma (St. Louis, Mo.). Tris (2,2'-bipyridyl)ruthenium(II) chloride, $Ru(bpy)_3^{2+}$, was procured from Alpha Products (Danvers, Mass.). ECL-related reagents were obtained from IGEN, Inc., (Rockville, Md.).

EXAMPLE 1

Quantitative Detection of Hydrogen Peroxide

Hydrogen peroxide reacts with oxalate to produce water and carbon dioxide. The fact that oxalate generates a carbon dioxide radical anion, a strong reductant, upon oxidation at the electrode, is the basis of this assay. The presence and quantity of hydrogen peroxide can, therefore, be measured and detected based on the reduction in ECL intensity. Thus, aqueous solutions of hydrogen peroxide (20 µL of 2–100 mmol/L stock) and oxalate (30 µL of 5 mmol/L, Ru(bpy)32+ (25 µL of 12 µmol/L, containing 0.06% Triton X-100 buffer (120 µL of 100 mmol/L phosphate, pH 5.0 containing 0.05% Triton X-100) were mixed in 12×75 mm polypropylene tubes, placed in the Origen™ analyzer and the ECL was measured.

Figure 2A:
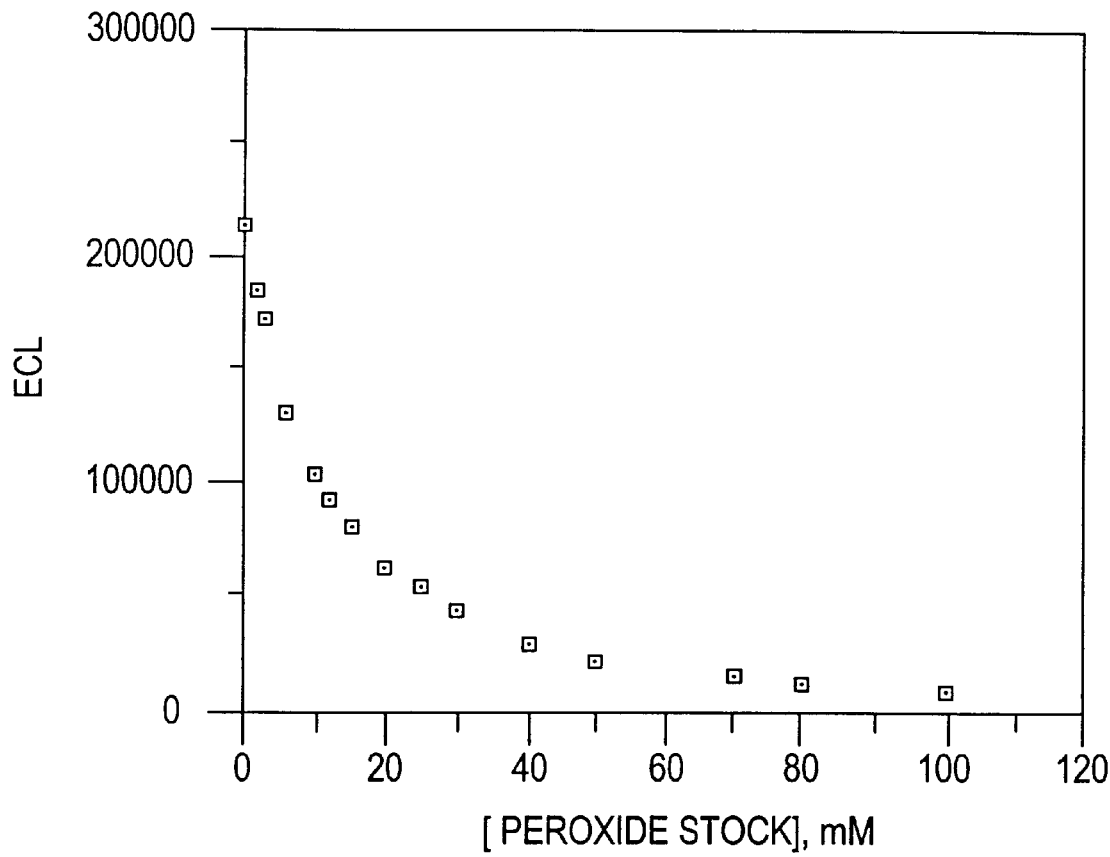
FIG. 2. ECL determination of hydrogen peroxide.
Figure 2B:
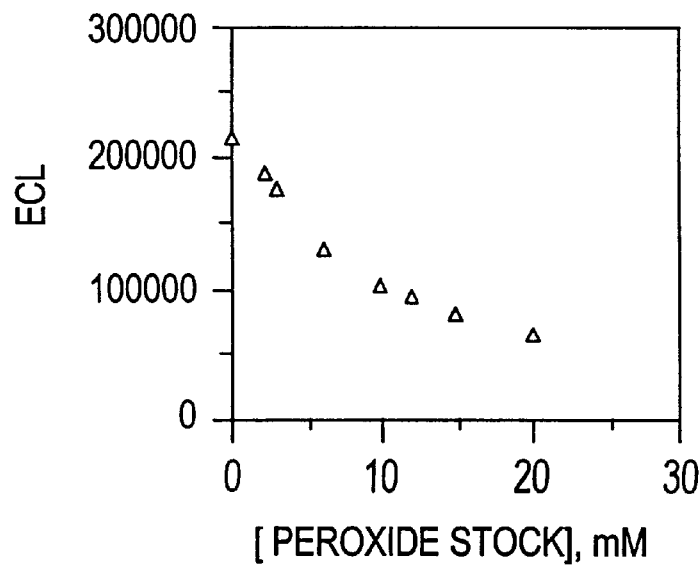

For the detection of peroxide, stock concentrations of 2–100 mM were examined using fixed oxalate (500 µmol/L) and Ru(bpy)$_3^2$+(1 µmol/L) concentrations. The expected decrease in ECL intensity with increasing peroxide concentration was observed (FIG. 2a).

EXAMPLE 2

Cholesterol Determination ($H_2O_2$)

Catalase

In order to insure the presence of sufficient oxygen for the cholesterol oxidase catalyzed reaction, hydrogen peroxide was converted to oxygen using catalase. An aqueous solution containing catalase (4 µL of 10 mg/mL), hydrogen peroxide (10 µL of 100 mmol/L) and buffer (947 µL of 100 mmol/L phosphate, pH 7.9, containing 0.05% Triton X-100) was admixed in a 1-mL quartz cuvette (1-cm light path), and incubated at 25° C. for 5 minutes. The instrument was zeroed, cholesterol oxidase (8 µL of 48 U/mg) was added and the instrument was re-zeroed. An aqueous solution of cholesterol calibrator (4 µL, Sigma) was added, and the rate of change of absorbance measured at 25° C. for 30 minutes. Also, according to the above reaction, the presence or absence of catalase itself may be monitored by ECL monitoring of the consumed hydrogen peroxide.

Aqueous solutions of cholesterol oxidase (10 µL of 48 mg/mL), oxalate (60 µL of 10 mmol/L), Ru(bpy)$_3^2$+ (25 µL of 12 µM containing 0.6% Triton X-100), and cholesterol standards (30 µL of 2–50 mmol/L prepared by dissolving cholesterol in 60% Triton X-100/ethanol) in phosphate buffer (pH 5.0, containing 0.05% Triton X-100) were incubated at 25° C. for 10 minutes. The solutions were inserted into an Origen analyzer and the ECL was measured.

Cholesterol Oxidase

The assay for cholesterol oxidase is based on the conversion of cholesterol to cholest-4-en-3-one which is detected spectrophotometrically at 240 nm due to conjugation the steroid A ring.

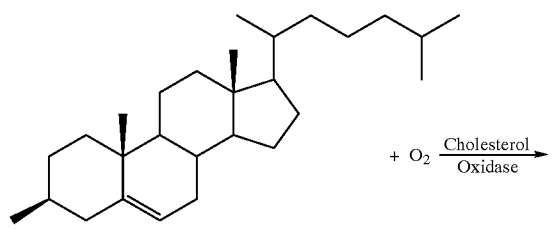

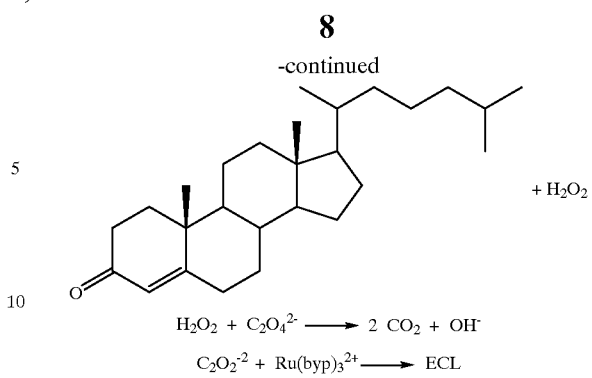

$H_2O_2 + C_2O_4^{2-} \longrightarrow 2\ CO_2 + OH^-$ $C_2O_2^{-2} + Ru(byp)_3^{2+} \longrightarrow ECL$ Cholesterol oxidase (8 µL of 48 U/mg) and buffer (972 µL of 100 mmol/L phosphate, pH 7.5, containing 0.05% Triton X-100) were mixed, by inversion, in 1.0 mL cuvette (1-cm light path) and the instrument was zeroed. An aqueous solution of cholesterol calibrator (20 µL. Sigma) was added and the rate of change of absorbance monitored at 240 nm for 20 minutes at 25° C. The molar absorptivity coefficient for cholest-4-en-3-one used was 15,000 $M^{-1}\text{-cm}^{-1}$.

Detection of Cholesterol

Figure 3A:
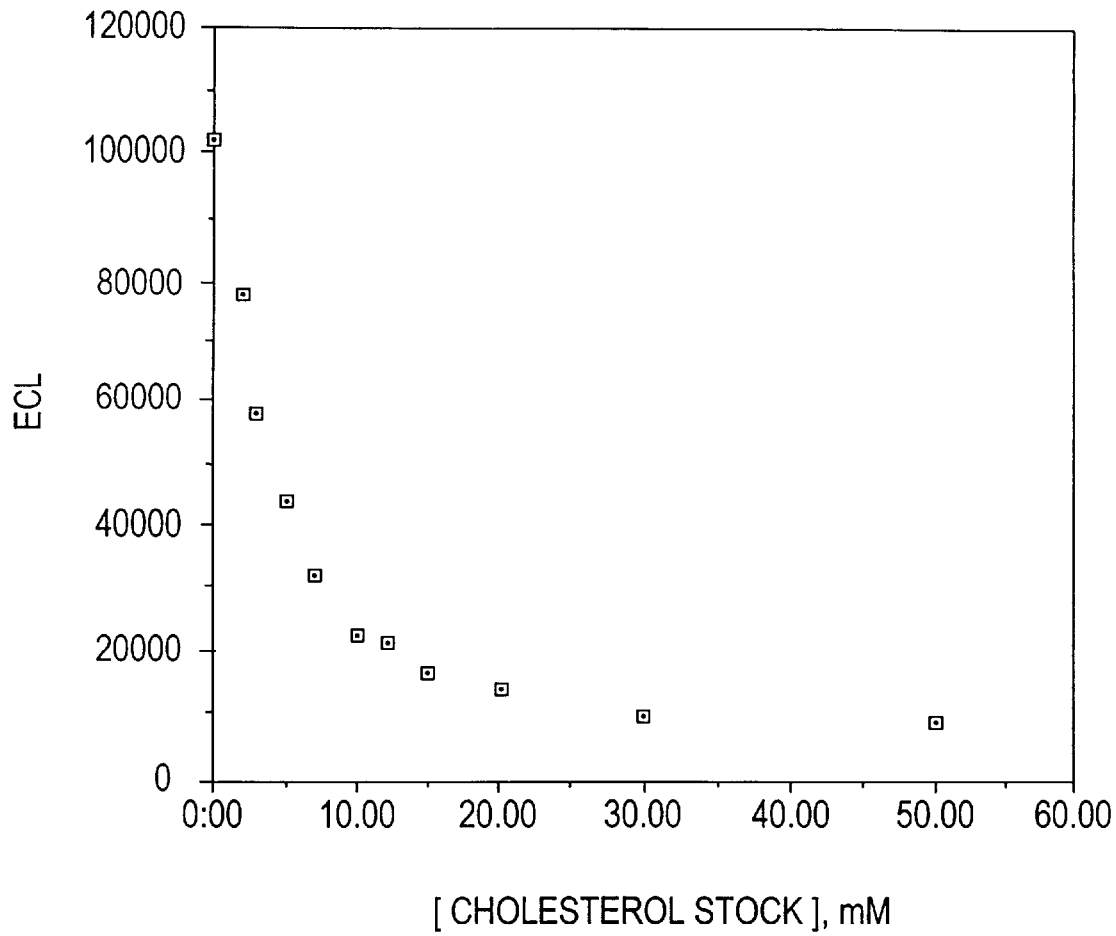
FIG. 3. ECL-Based determination of cholesterol.
Figure 3B:
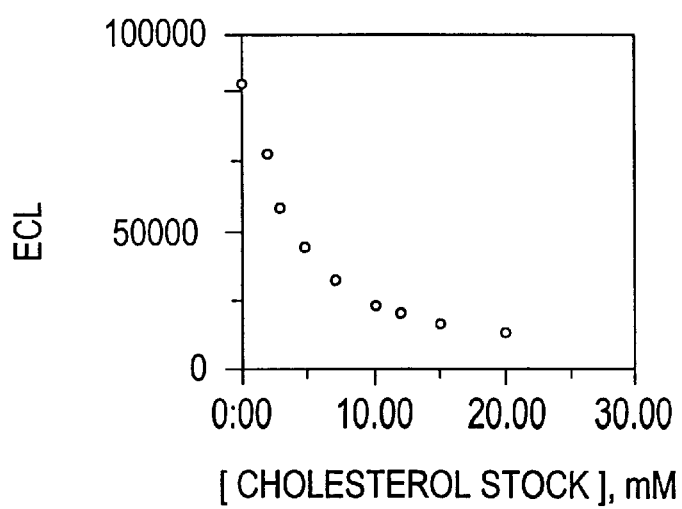

The assay for cholesterol is based on the principle that hydrogen peroxide is produced by the enzymatic action of cholesterol oxidase on cholesterol. The hydrogen peroxide so formed is detected by its reaction with oxalate. Employing a similar procedure as above, aqueous solutions of cholesterol oxidase (10 µL of 48 U/mg), oxalate (60 µL of 10 mmol/L, Ru(bpy)$_3^{2+}$ (25 µL of 12 µmol/L, containing 0.6% Triton X-100) and cholesterol reagent (30 µL of 2–50 mmol/L, prepared by dissolving cholesterol in a Triton X-100-ethanol 3:2 v/v mixture) in buffer (120 µL of 100 mmol/L phosphate, pH 5.0, containing 0.05% Triton X-100) were mixed, inserted into the Origen analyzer and the ECL was measured. ECL-based determination of cholesterol is shown in FIG. 3.

Cholesterol Assay

The principle for this determination is based on the enzymatic action of cholesterol oxidase on cholesterol to produce cholest-4-en-3-one and hydrogen peroxide below

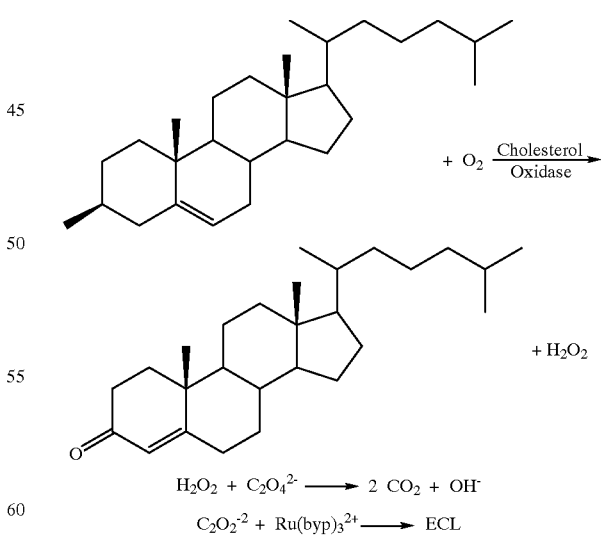

$H_2O_2 + C_2O_4^{2-} \longrightarrow 2\ CO_2 + OH^-$ $C_2O_2^{-2} + Ru(byp)_3^{2+} \longrightarrow ECL$ The hydrogen peroxide so formed reacts with oxalate in an equimolar stoichiometry. The remaining oxalate then reacts with Ru(bpy)$_3^{2+}$ which is electrochemically oxidized.

The observed ECL intensity directly relates to the amount of reductant, in this case, oxalate, which, in turn, is inversely proportional to the amount of cholesterol present. Primary concerns with regard to peroxide, and ultimately cholesterol determination, included the efficiency of cholesterol oxidase at different pH values, and the optimum conditions for maximum light generation using oxalate. The enzyme has a pH optimum of 7.5, while oxalate gives the strongest ECL signal at pH 5. Consequently, spectrophotometric assays were performed at pH values of 5.0 and 6.0. The results suggested that the activity of the enzyme was identical at both pH values examined (data not shown).

A secondary concern was the behavior of cholesterol oxidase in the absence of catalase. Plots depicting change in absorbance versus cholesterol concentration, with and without catalase, gave identical results, suggesting that the buffer is sufficiently saturated with oxygen for the oxidase reaction to proceed (data not shown).

For cholesterol detection, solution concentrations within the clinical range (2–50 mmol/L), were examined (FIG. 3). The problem of cholesterol solubilization was solved by dissolution in a Triton X-100/ethanol mixture. As in the case with peroxide, the same inverse relationship between ECL and concentration was seen. It was also observed that varying the oxalate concentration (100 μmol/1–2 mmol/L) increased the sensitivity of the assay.

EXAMPLE 3

Glucose determination

Figure 4A:
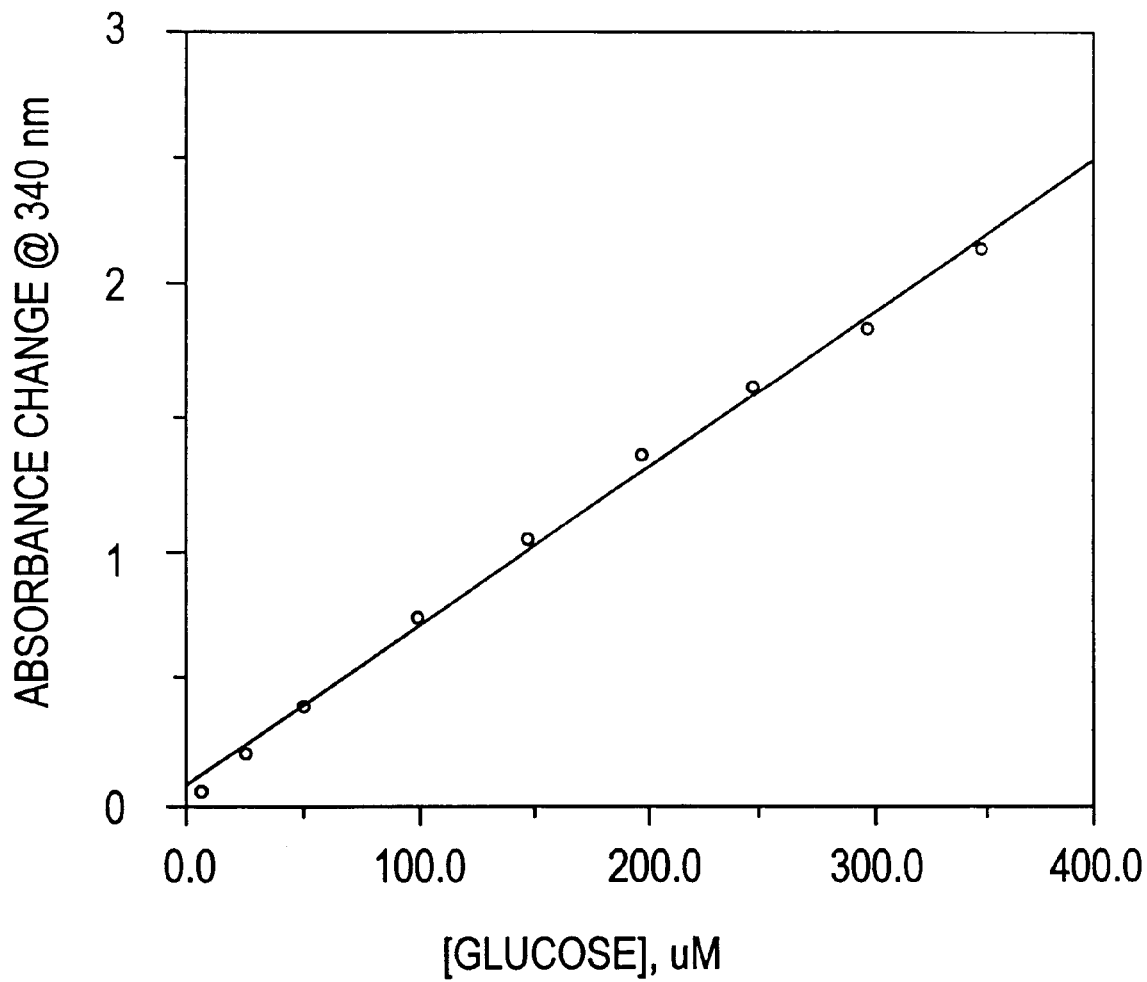
FIG. 4a. Shows the spectrophotometric determination of glucose (Sigma).
Figure 4B:
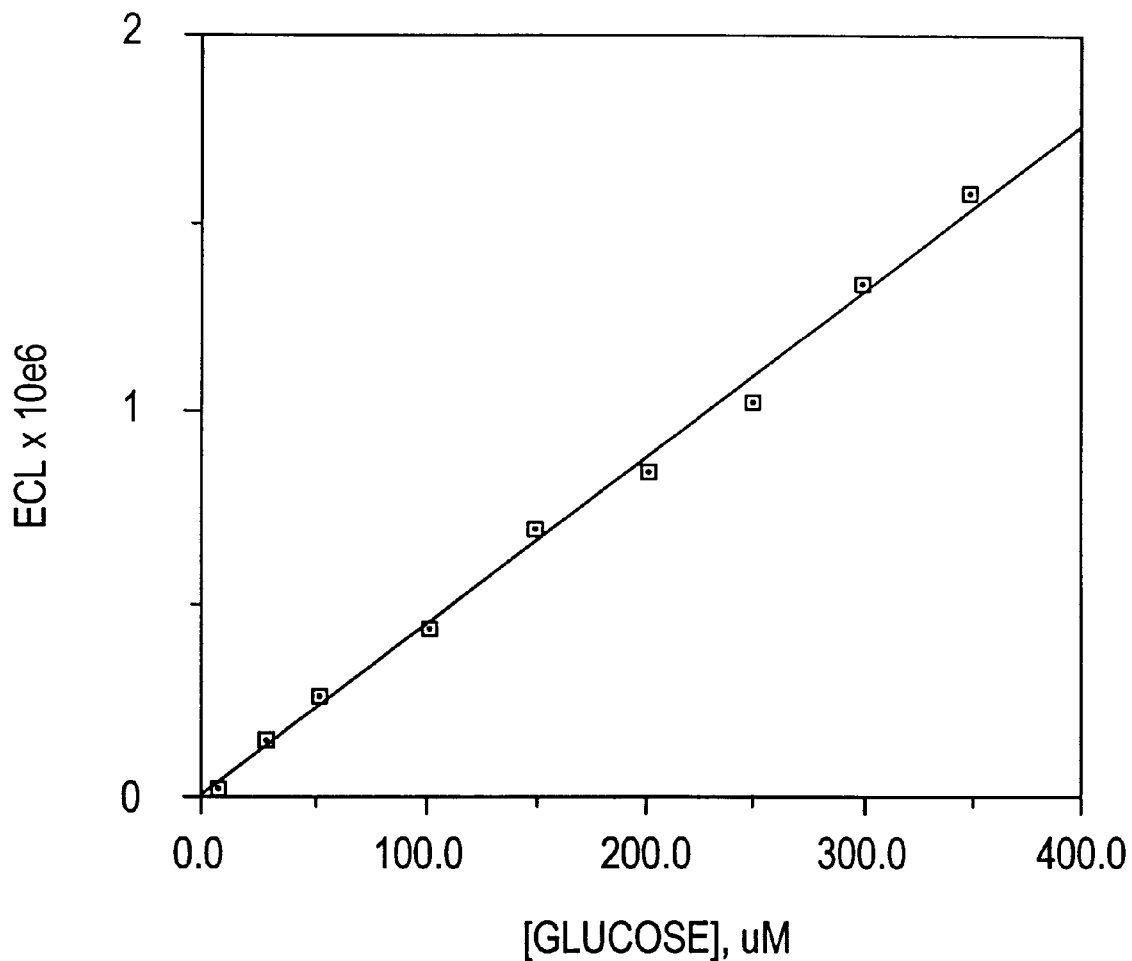
FIG. 4b. Shows the ECL-Based determination of glucose.
Figure 4C:
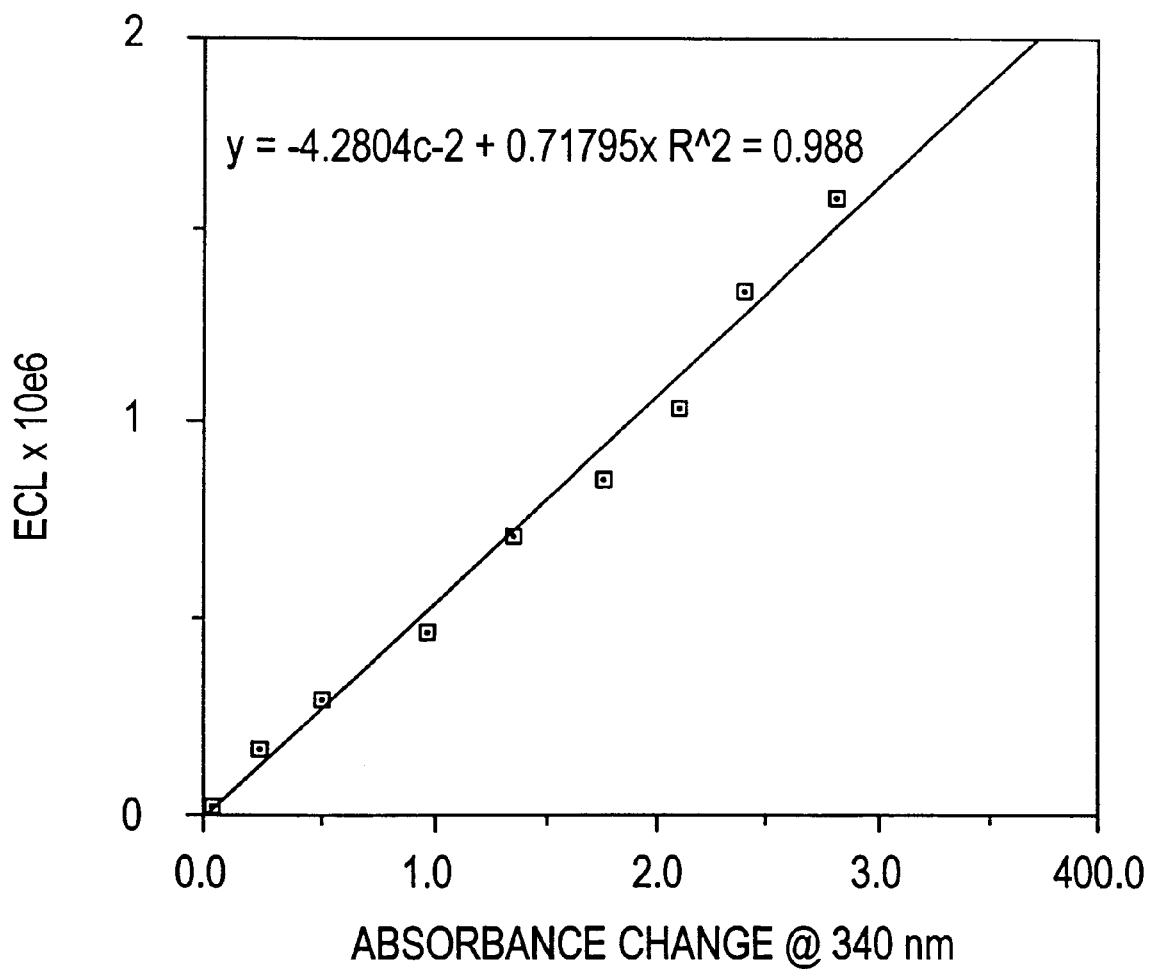
FIG. 4c. Shows the spectrophotometric and ECL correlation for glucose.

A solution of glucose oxidase (25 μL of 3.0 mg/mL in water) and freshly prepared B-D-(+)-glucose (25 μL of 1 to 50 mmol/L in water) was incubated at 25° C. for 15 minutes in phosphate buffer (75 μL of 10 mmol/L, pH 5.0, containing 0.05% Triton X-100). The solution was diluted (to 300 uL) with a cocktail containing $Ru(bpy)_3^{2+}$ (25 μL of 12 μmol/L in water) and oxalate (30 μL of 10 mmol/L in water), in acetate buffer (120 μL of 100 mmol/L, pH 5.0, containing 0.05% Triton X-100). The solutions were inserted into the Origen analyzer and the ECL was measured. FIGS. 4a–4c respectively show the spectrophotometric determination of glucose, the ECL determination of glucose and a comparison of the two techniques.

Glucose Assay

Figure 4D:
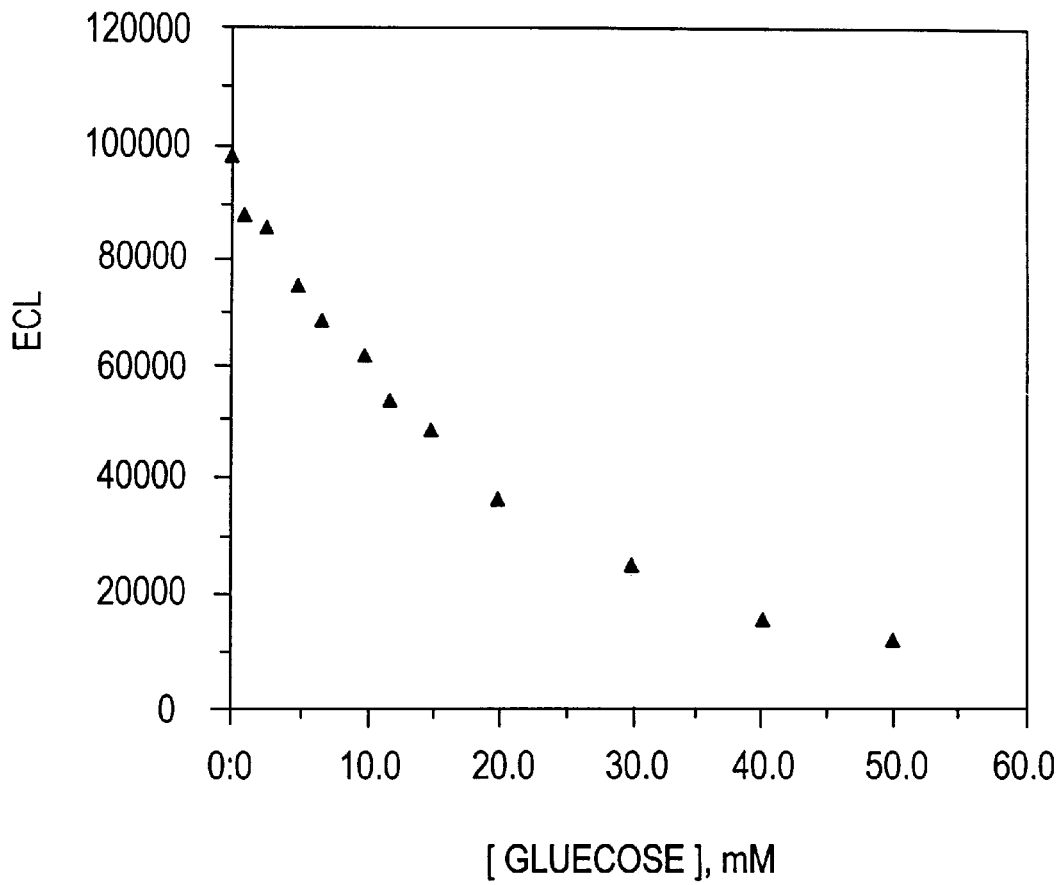
FIGS. 4d–4e. ECL-Based determination of glucose.
Figure 4E:
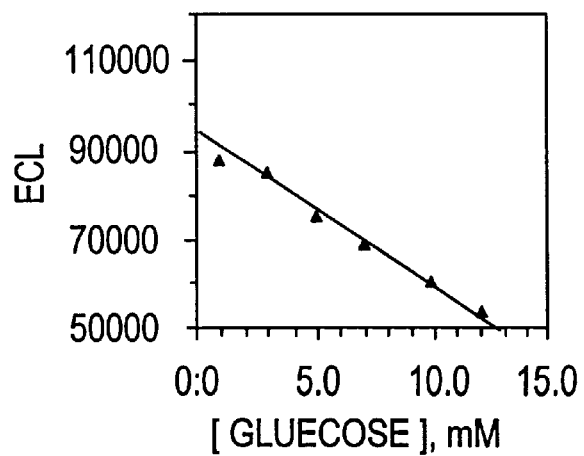

Glucose was quantitated in a similar fashion to cholesterol. The hydrogen peroxide produced from the action of glucose oxidase on β-D-glucose was coupled to a $Ru(bpy)_3^{2+}$ oxalate system. The same inverse relationship between ECL and glucose concentration was observed (FIG. 4d). Due to the different pH requirements of the enzyme (pH 6.0) and oxalate (pH 5.0), the reaction was conducted in two stages. It was observed that reactions performed at pH 6.0 generated very low ECL signals. Consequently, the enzymatic reaction was allowed to go to completion, then the mixture diluted with an oxalate-luminophore solution. This led to significantly larger ECL counts.

Although the invention has been described in conjunction with the specific embodiments, it is evident that many alternatives and variations will be apparent to those skilled in the art in light of the foregoing description. Accordingly, the invention is intended to embrace all of the alternatives and variations that fall within the spirit and scope of the appended claims. Further, the subject matter of the above cited United States Patents are incorporated herein by reference.

What is claimed is:

1. An ECL emission composition comprising (1) an $H_2O_2$-producing or -consuming reactant which produces or consumes $H_2O_2$ in the absence of an applied electrical potential, (2) a coreactant which reacts with $H_2O_2$, and (3) a metal, colorimetric luminophore that emits light from the reaction between components (2)–(3), in the presence of an oxidizing or reducing electrochemical potential, with the proviso that when (1) contains an $H_2O_2$-consuming reactant, $H_2O_2$ is also present.

2. A composition capable of emitting electrochemiluminescence comprising:

(a) at least one species selected from the group consisting of:
  (i) $H_2O_2$,
  (ii) an $H_2O_2$ producing reactant, and
  (iii) an $H_2O_2$ consuming reactant, wherein species (iii) is in the presence of $H_2O_2$ and species (ii) and (iii) produce or consume $H_2O_2$ in the absence of an applied electrical potential, (b) a luminophore capable of being induced to electrochemiluminesce;

(c) an ECL coreactant for said luminophore wherein said ECL coreactant reacts with $H_2O_2$.

3. A composition according to claim 2, wherein said luminophore is $Ru(bpy)_3^{+2}$.

4. A composition according to claim 2 wherein said $H_2O_2$ producing reactant or said $H_2O_2$ consuming reactant is at least one substrate that when acted upon by an enzyme produces or consumes $H_2O_2$.

5. A composition according to claim 2 wherein said reactant, (ii) and/or (iii), is selected from the group consisting of cholesterol, glucose, a triglyceride, glycerol-1-phosphate oxidase, uric acid and ethanol.

6. A composition according to claim 2 wherein said coreactant is an oxalate.

7. A composition according to claim 2 wherein said $H_2O_2$ producing or consuming reactant is at least one enzyme that reacts with a substrate to produce or consume $H_2O_2$.

8. A composition capable of emitting electrochemiluminescence comprising:

(a) at least one species selected from the group consisting of:
  (i) $H_2O_2$,
  (ii) an $H_2O_2$ producing reactant, and
  (iii) an $H_2O_2$ consuming reactant, wherein species (iii) is in the presence of $H_2O_2$ and species (ii) and (iii) produce or consume $H_2O_2$ in the absence of an applied electrical potential, (b) a luminophore capable of being induced to electrochemiluminesce;

(c) an ECL coreactant for said luminophore wherein said ECL coreactant reacts with $H_2O_2$, and said coreactant is oxalate.

* * * * *